United States Patent [19]

Smith

[11] Patent Number: 5,377,510

[45] Date of Patent: Jan. 3, 1995

[54] KEY-RELEASABLE RESTRAINT

[75] Inventor: Jerry Smith, Littleton, Colo.

[73] Assignee: The McKinley Group, Littleton, Colo.

[21] Appl. No.: 977,518

[22] Filed: Nov. 17, 1992

[51] Int. Cl.$^6$ ............................................... A61F 5/37
[52] U.S. Cl. ...................................... 70/16; 128/878; 24/16 PB
[58] Field of Search ......................... 24/16 PB, 30.5 P; 70/15–18, DIG. 9; 128/869, 876, 877, 878, 879, 880, 881, 882

[56] References Cited

U.S. PATENT DOCUMENTS

| | | | |
|---|---|---|---|
| 381,005 | 4/1988 | Ferrell | 70/18 |
| 1,462,238 | 5/1922 | Mennillo | 70/15 |
| 3,933,015 | 1/1976 | Balicki | 70/18 |
| 4,287,731 | 9/1981 | Kruger | 70/16 |
| 4,909,051 | 3/1990 | Lee | 70/16 |
| 5,088,158 | 2/1992 | Burkholder | 70/16 |
| 5,099,662 | 3/1992 | Tsai | 70/16 |
| 5,159,728 | 11/1992 | Bingold | 70/16 |
| 5,193,254 | 3/1993 | Geisinger | 70/16 |

Primary Examiner—Mickey Yu
Assistant Examiner—David Kenealy
Attorney, Agent, or Firm—Beaton & Swanson

[57] ABSTRACT

A device for establishing an adjustable and flexible loop to act as releasable cuffs to restrain a person or to act as a releasable tie for bundles of wire or cable. A strap includes a free end and a lock end to receive the free end to establish a loop. The lock has a ratchet with a set of pawls engageable with the teeth spaced along the free end of the strap. The ratchet is hingedly mounted in the lock so that urging the strap into the lock causes the teeth to apply a rotational force to the pawls which rotates the ratchet about the hinge to disengage the pawls from the teeth to allow the strap to be inserted into the lock, while urging the strap out of the lock causes the teeth to apply an opposite rotational force to the pawls which rotates the ratchet about the hinge in the opposite direction to engage the pawls with the teeth to prevent the strap from being withdrawn. The lock includes a keyhole to receive a key with a tab, so that the rotation of the key causes the tab to apply a force rotating the ratchet about the hinge to disengage the pawls from the teeth to allow the strap to be withdrawn.

3 Claims, 2 Drawing Sheets

KEY-RELEASABLE RESTRAINT

FIELD OF THE INVENTION

The present invention relates to the field of restraining devices, in particular restraining devices that are flexible and accommodate variable-sized objects in a bundling manner. The device is especially useful as flexible cuffs to restrain a personn but also has utility in bundling cables or wires or in securing other objects together.

BACKGROUND OF THE INVENTION

The use of flexible straps to secure bundles of wire or cable is well-known. Typical devices using this concept consist of an elongated strap with a lock on one end. The strap is placed around the bundle of wire or cable to be secured, to form a loop, and then the free end of the strap is inserted into the lock and the loop is tightened. The lock generally includes a ratchet arrangement which engages a set of teeth or serations on the free end of the strap. Therefore, once the loop is tightened by drawing the free end of the strap through the lock, the engagement of the ratchet with the teeth or serations maintain the tightened condition. Such devices are commonly referred to as "cable ties".

Cable ties have a number of distinct advantages for securing bundles of wire or cable. Cables ties accommodate bundles of varying sizes and shapes. Thus, a very wide range of bundle sizes and shapes can be secured by a worker with only a few sizes of cable ties in his toolbox. Also, because the loop which secures the bundle is not formed until the worker inserts the free end of the strap into the lock, there is no need to thread the wire or cable through an already-closed loop; the strap is simply looped around the bundle that is to be secured. This also allows the bundle that is to be secured to be easily attached to other elements such as structural members in the vicinity of the wire or cable installation, by simply including those members in the loop where it is formed. Cable ties are also generally made of lightweight plastic so that hundreds of them may weight only a few pounds.

One of the chief advantages of cable ties over other devices for securing bundles of wire or cable is that they can be installed with a tension in the looped strap which ensures a tight and secure installation. The worker simply pulls the free end of the strap tightly through the lock on the other end to diminish the loop size. As he does so, the ratchet in the lock ratchets through the teeth or serations in the free end. When the free end is let loose, it cannot back out of the lock and thereby expand the size of the loop by more than the small distance between adjacent teeth or serations which is generally less than a tenth of an inch.

It has been known for some time that cable ties and similar devices employing flexible straps that are adjustably looped into locks that use one-way ratchets, could be used as cuffs to restrain a person. The simplest way to restrain a person using a cable tie is to loop a single cable tie around the person's wrists and tighten the loops so that the wrists are bound together. This is particularly effective if the person's hands are behind his back. Additional restrain can be established by looping another cable tie around the person's ankles and tightening that loop to bind the ankles together. Law enforcement authorities have used cable ties for this purpose for a number of years in place of traditional metal hand cuffs, because in comparison to metal hand cuffs, cable ties are lightweight and compact. Also, a danger of metal handcuffs is that the person to be strained may break free after one cuff is on but before the second cuff is on, and then the free cuff becomes a deadly swinging weapon.

Devices have also been developed which operate on the basic idea of a free strap looped into a ratcheting lock, but which are specifically configured for restraining a person rather than for bundling wire or cable. For example, U.S. Pat. No. 4,071,023 by Gregory is a restraining cuff with two free straps and two ratcheting locks, so that there is a separate cuff for each of two wrists or two ankles. U.S. Pat. No. 5,088,148 by Burkholder is similar to the Gregory patent in that there are two free straps and two ratcheting locks so that two cuffs can be formed, but the two locks are positioned on a single mount. U.S. Pat. No. 5,099,662 by Tsai includes a mechanism to release the ratchet to allow the device to be re-used. Similarly, U.S. Pat. No. 4,964,419 by Karriker includes a mechanism to expand and contract the cuff size.

A significant drawback to the use of ordinary cable ties as restraining devices is that most of them can be used only once. After the free end of the strap is looped into the ratcheting lock, it is impossible to draw it back out. Therefore, it is necessary to cut the strap with a pair of wire cutters or a similar tool when the restrained person is to be freed. In fact, it is necessary to cut the strap and apply another cable tie if the person is not to be freed but merely because the loop was too tight on the person. Of course, this destroys the cable tie.

There are a few devices which are re-usable such as the Karriker devices mentioned above. However, a drawback to those devices is that they are designed such that the lock can be released without the use of a key so that the strained person himself or someone else without authority can release them. Also in the prior art are ordinary cable ties not specifically designed to restrain a person, that have a tab protruding out of the ratcheting lock to disengage a ratchet pawl from teeth on the strap to release the strap. Such devices have the same limitations as the Karriker device in that there is nothing to prevent unauthorized persons from releasing the device. The Tsai device mentioned above is releasable using a key; however, unlike the present invention, that device is quite complex in its mechanism.

DETAILED DESCRIPTION OF THE INVENTION

Figure 1:
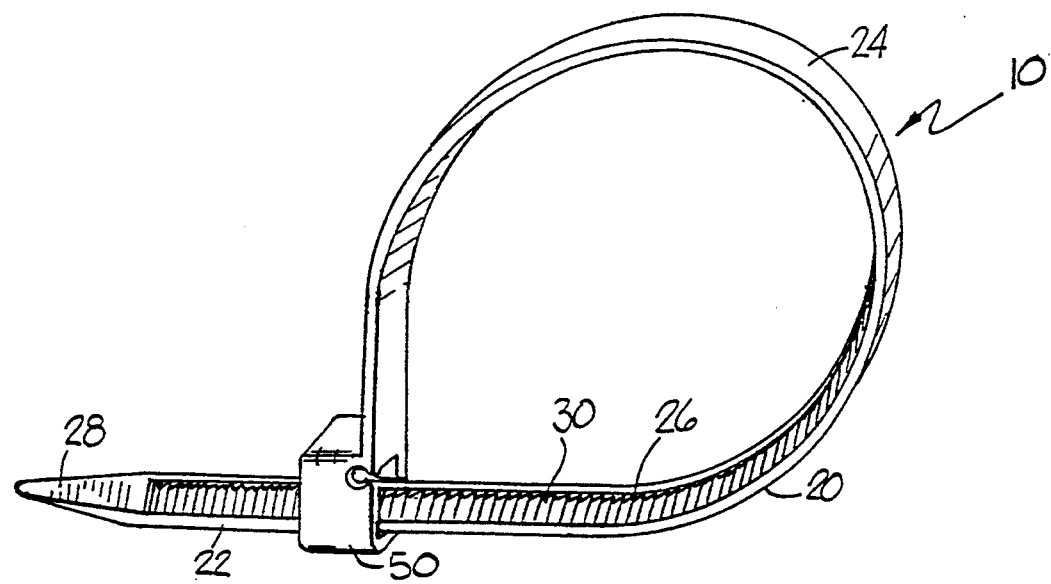
FIG. 1 is a pictorial view of the present invention, with the free end of the strap looped into the locking end of the strap.

A pictorial view of the invention 10 is shown in FIG. 1, in which the invention is looped together to form a restraint. The principal elements of the invention 10 include a strap 20 having a free end 22 and having a ratcheting lock 50 at the end opposite the free end. The strap has a surface 24 on the outside of the loop that may be substantially smooth and a surface 26 on the inside of the loop that includes a series of teeth 30 which are described in more detail below. The free end 22 of the strap 20 may include a tip 28 which is tapered from side to side and through its width relative to the rest of the strap to assist in threading the tip 28 through the ratcheting lock in the manner described below.

Figure 2:
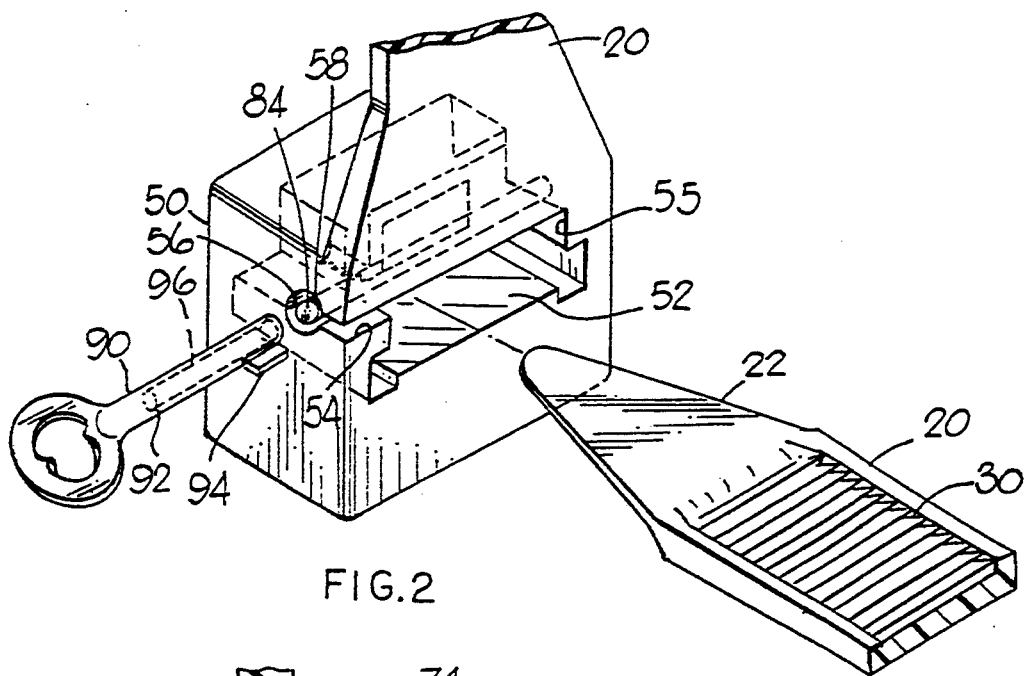
FIG. 2 is a perspective view showing the lock of the present invention in detail.

The lock 50 is shown in more detail in the enlarged view of FIG. 2 which also shows the key 90. The lock includes a strap slot 52 to receive the free end 22 of the strap 20. The strap slot 52 is open at the top and joins a keyhole 58 which includes a round portion 56 and a keyslot portion 54. Between the keyslot 54 and the strap slot 52, and joining those two slots is an open portion 55 which allows the key to turn in the manner described below. The key 90 includes a barrel 92 and a tab 94 which are received by the keyhole 56 and keyslot 54, respectively. A pin 84 extends through and is coaxial with the keyhole 54, and is received by a hole 96 in the barrel of the key 90 when the key is inserted into the keyhole.

Figure 3:
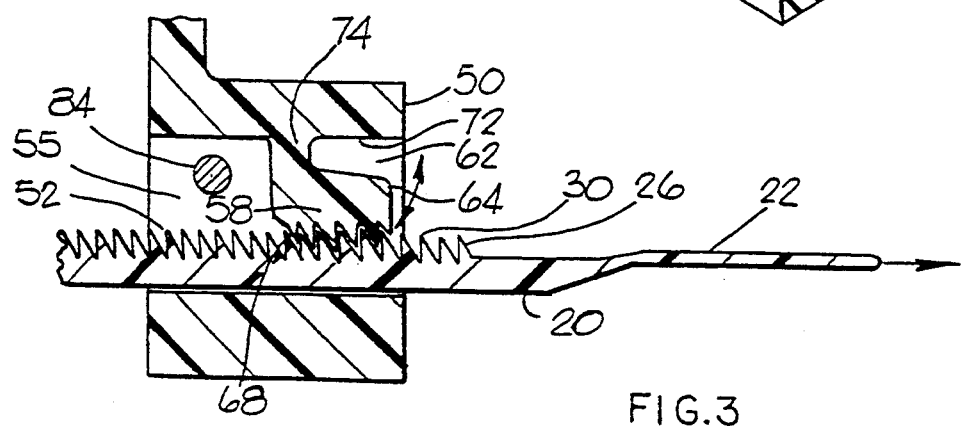
FIG. 3 is a sectional view of the lock of the present invention, with the free end of the strap inserted therein.

A cross-sectional view of the lock 50 with the free end 22 of the strap 20 is shown in FIG. 3 which also shows the ratcheting system internal to the lock. The lock includes an internal cavity 62, the bottom of which includes the strap slot 52. Positioned within the cavity 62 is a ratchet body 64 with a set of ratchet pawls 68 on the bottom to engage the teeth 30 on the interior surface 26 of the strap 20. The pawls 68 are sized and spaced approximately the same as the teeth 30 so that several pawls can engage several teeth at once. The ratchet body 64 is attached to the body of the lock 50 at the upper wall 72 of the cavity 62 by a flexible hinge 74 which may be plastic material welded or adhered to the upper wall 72 and the ratchet body 64, or preferably may be integrally molded so that the ratchet body 64, the lock 50 and the hinge 74 are all a single integral element, the hinge 74 being sized and of a flexibility such that it allows the ratchet body 64 to move up and down as shown by the arrows as the hinge flexes and unflexes.

It can be appreciated from FIG. 3 that the free end 22 of the strap 20 can be inserted into the lock in the direction shown. As the strap moves into the lock and through the strap slot 52, the teeth 30 on the strap 20 engage the pawls 68 on the ratchet body 74 and urge the pawls 68 counter-clockwise about the point of pivot at the hinge 74. The hinge 74 accommodates this urging by flexing to allow the ratchet body 64 to move upward and away from the teeth 30 to allow the teeth and the strap 20 to pass. This is a somewhat discontinuous process, for the movement of the strap 20 through the lock 50 causes the teeth 30 to "click" a tooth at a time past the pawls 68 as the ratchet body 64 moves up and down through the flexing and unflexing of the hinge 74. This clicking is useful in indicating the progression of the strap 20 through the lock 50 and the consequential tightening of the loop formed by the strap.

If one attempts to withdraw the strap 20 from the lock 50 by pulling the strap 20 out of the strap slot 52, the strap teeth 30 urge the pawls counter-clockwise about the pivot point of the hinge 74. This urging is initially accommodated by the flexing of the hinge 74 to allow the ratchet body to move downward and toward the strap 20. However, before a single tooth 30 can pass and disengage from the pawls 68, this downward movement of the ratchet body 74 jams the ratchet body 74 against the strap 20. Thus the withdrawal of the strap 29 is prevented.

Figure 4:
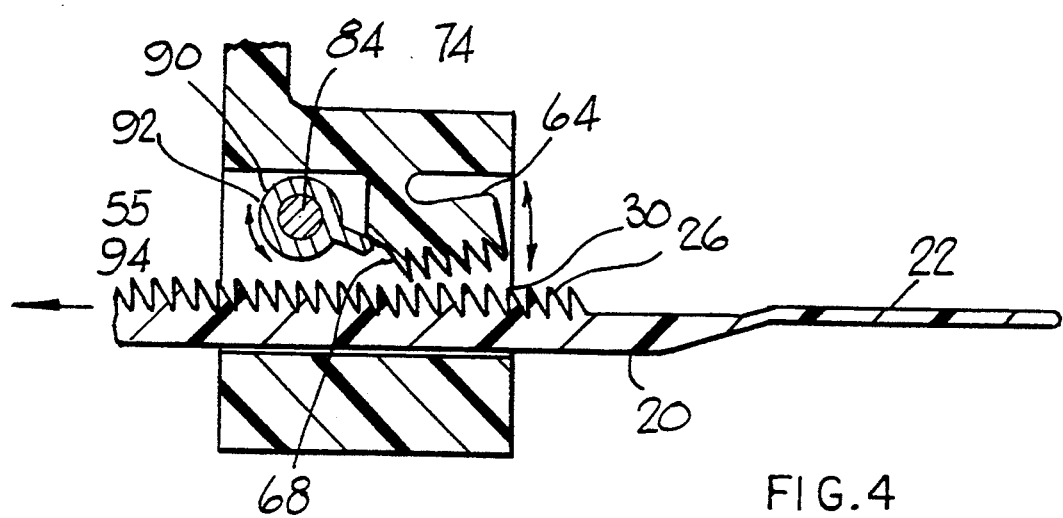
FIG. 4 is a sectional view of the lock of the present invention, with the free end of the strap inserted therein and with key operating upon the ratchet mechanism of the lock.

The strap 20 can be released from the lock 50 in the manner shown in FIG. 4. The lug 90 is inserted into the lock 50 so that the barrel 92 passes into the keyhole 56 and the barrel hole 96 is received by the pin 84. The tab 94 is received by the keyslot 54. Once the key 90 is fully inserted, the tab 94 is positioned within the open portion 55 between the strap slot 52 and the key slot 54. The key can then be rotated, counter-clockwise in the view shown, so that the tab 94 moves through that open portion 55 until it bears against the ratchet body 64. By continuing to rotate the key counter-clockwise to urge the ratchet body counter-clockwise about the pivot point of the hinge 74. The hinge 74 accommodates this urging by flexing to allow the ratchet body to rotate counterclockwise about the hinge 74, thereby moving the ratchet body upward so that the pawls 64 disengage the teeth 30. Once the pawls are disengaged from the teeth 30, the strap 20 is free to be withdrawn from the lock 50. Thus the device can be released from the locked position, or adjusted or re-used any number of times.

What is claimed is:

1. A key-releasable restraining device, comprising: a flexible strap having a lock integral with the strap and located on one end of the strap, a free end opposite the end with the lock for insertion into the lock to form an adjustable loop, and a set of strap teeth spaced along the strap; the lock including a cavity through which the strap passes, the cavity being bounded by a wall on one side to receive the strap and a ratchet-mounting wall on the opposite side, and the lock further including a one-way ratchet integrally formed with the lock having a body spaced apart from the ratchet-mounting wall, the body having a free end and a hinge end opposite the free end, and a hinge extending from the hinge end of the body to the ratchet-mounting wall, and a set of ratchet teeth normally engaging the strap teeth to allow the strap teeth to pass the ratchet in a first direction as the strap is inserted into the lock but not in a second direction opposite the first direction when the strap is urged out of the lock; and a key-operated ratchet release to disengage the ratchet teeth from the strap teeth to allow the strap teeth to pass the ratchet teeth in said second direction to allow the strap to be withdrawn from the ratchet, the ratchet release including a keyhole to receive a key, the keyhole having a hole portion to receive a barrel of a key and a slot portion to receive a tab of a key, the keyhole being positioned such that the insertion of the key into the keyhole and the subsequent rotation of the key causes the tab to apply a force against the hinge end of the ratchet body to rotate the ratchet about the hinge to disengage the ratchet teeth from the strap teeth to allow the strap to be withdrawn from the lock.

2. The device of claim 1, further comprising said key.

3. The device of claim 2, wherein the keyhole includes a pin co-axial with the hole portion, and the key includes a hole co-axial with the barrel to receive said pin when the key is inserted into the keyhole.

* * * * *